United States Patent

Krevolin et al.

[11] Patent Number: 5,112,336
[45] Date of Patent: May 12, 1992

[54] DRILL GUIDE AND TEMPLATE FOR PROSTHETIC DEVICES

[75] Inventors: Janet L. Krevolin, Austin; Steven G. Brown, Plugerville, both of Tex.

[73] Assignee: Intermedics Orthopedics, Inc., Austin, Tex.

[21] Appl. No.: 699,737

[22] Filed: May 14, 1991

[51] Int. Cl.⁵ ............................................. A61F 5/04
[52] U.S. Cl. ........................................ 606/96; 606/87
[58] Field of Search ............... 606/54, 53, 86, 87, 606/96–99, 101–105

[56] References Cited

U.S. PATENT DOCUMENTS

| | | | |
|---|---|---|---|
| 3,945,377 | 3/1976 | Kronner | 606/96 |
| 4,275,893 | 6/1981 | Bilanceri | 606/104 X |
| 4,299,212 | 11/1981 | Goudfrooy | 606/96 X |
| 4,803,976 | 2/1989 | Frigg et al. | 606/97 |
| 4,841,975 | 6/1989 | Woolson | 606/96 X |
| 5,019,077 | 5/1991 | De Bastiani et al. | 606/54 |

OTHER PUBLICATIONS

Richards Medical Brochure 1989.
Bigliani, et al., "Prosthetic Replacement of Acute Fractures of the Proximal Humerus", *Seminars in Arthroplasty*, vol. 1, No. 2, Oct. 1990, pp. 129–137.

*Primary Examiner*—Robert A. Hafer
*Assistant Examiner*—Brian E. Hanlon
*Attorney, Agent, or Firm*—John R. Merkling

[57] ABSTRACT

A drill guide and template for use in orthopedic surgery comprising a template and handle connected by a lockable universal joint. The handle further comprises a bent shaft. A template is provided with pins so that the template can be set into bone when accurately placed against a resected bony surface. The universal joint comprises a ball and socket joint with slots for increased adaptability. A threaded nut grips the ball against a distal end of the bent shaft. Tightening the nut onto shaft locks the ball in a selected position.

6 Claims, 2 Drawing Sheets

DRILL GUIDE AND TEMPLATE FOR PROSTHETIC DEVICES

BACKGROUND OF OUR INVENTION

Our invention relates to apparatus for performing orthopedic surgery and particularly for apparatus used in preparing bones of patients to receive prosthetic devices. In particular, our invention relates to a drill guide and template having a universal joint interposed between a handle and the template. The universal joint can be locked, providing great flexibility combined with stability. We have found our invention particularly useful for preparing the glenoid cavity of a shoulder, where access may be particularly constrained, but our invention is applicable to orthopedic procedures generally.

Orthopedic implants which replace diseased or broken joints are well-known. In recent years, however, implants have become increasingly complex and precise. Surgeons strive for accurate, replicable surgical techniques so that precise fits can be obtained. Increased contact between bone and prostheses has been found to increase long-term fixation. Jigs and guides can be used by surgeons for preparing the bone to receive prosthetic implants. Use of these guides may be constrained, however, by the surrounding soft tissue, muscles, and tendons of the patient, and by the technique of the particular surgeon. These limitations apply to all joint replacements, but they particularly relevant for shoulder replacements because the available operating room may be particularly restricted. An example of a glenoid prosthesis and surgical technique is described in U.S. Pat. No. 4,964,865 to Burkhead, et al., which patent is assigned to the assignee of our invention. To install the device described by Burkhead, a surgeon would resect a flat surface within the glenoid cavity against which a flat medial surface of the glenoid prosthesis would rest. The surgeon must also drill accurate holes for pegs. If the prosthesis is accurately mounted on the bone, the prosthesis will not rock against the bone and the joint would be less likely to fail. The surgeon should therefore, accurately prepare the glenoid surface to receive the prosthesis.

To prepare the surface, drill guides and templates have been used. In the past, however, these drill guides have generally been mounted with fixed handles. A fixed handle provides stability for the drill guide, but the drill guide cannot be easily adapted to the particular patient or the style of the attending surgeon. Examples of such drill guides available to surgeons are those produced by Biomet for their Biomodular(TM) Total Shoulder and Biangular (TM) Shoulder or by Richards Medical Company for their Cofield(TM) Total Shoulder System.

It is an object of our invention, therefore, to provide a drill guide for use in orthopedic surgery which can adapt to patient anatomy and surgical technique.

It is also an object of our invention to provide a drill guide which can be both adaptable and stable.

Another object of our invention is to provide a surgical drill guide with a handle which can be swiveled to a desired position and locked in position.

SUMMARY OF OUR INVENTION

We have invented a drill guide and template for use in orthopedic surgery comprising a template and handle connected by a lockable universal joint. The handle further comprises a bent shaft which, we have found, provides additional adaptability. A template is provided with pins so that the template can be set into bone when accurately placed against a resected bony surface. The universal joint comprises a ball and socket joint with slots for increased adaptability. A threaded nut grips the ball against a distal end of the bent shaft. Tightening the nut onto shaft locks the ball in a selected position. The drill guide of our invention is, therefore, both adaptable and secure so that accurate procedures may be performed under a variety of conditions.

These and other objects and features of our invention will be apparent to those skilled in the art from the following detailed description, made with reference to the accompanying drawings.

DETAILED DESCRIPTION OF OUR PREFERRED EMBODIMENT

Figure 1:
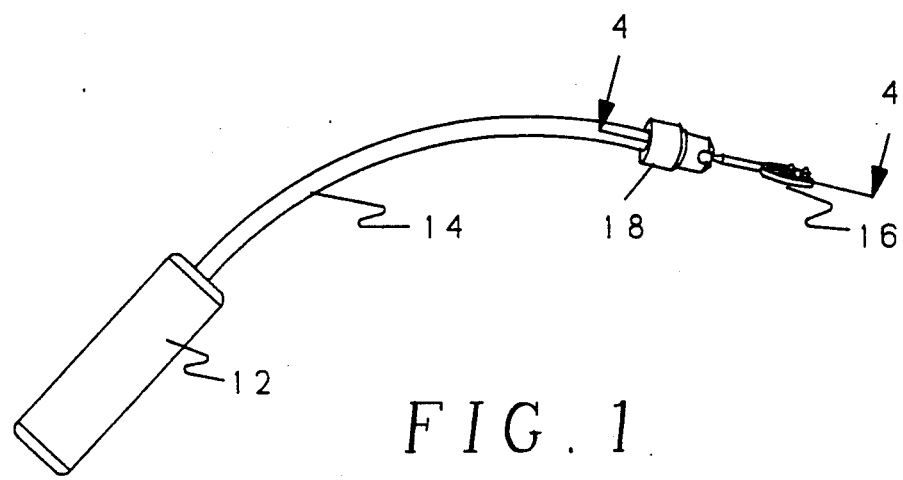
FIG. 1 is a perspective view of a drill guide and template according to our invention.

We will now describe our preferred embodiment of our invention by reference to the accompanying drawings. Like numerals have been used to designate like parts through out. We have invented a drill guide and template, generally designated 10, which comprises a handle 12 with a bent shaft 14 and a template 16. The shaft 14 and the template 16 are connected with a lockable ball and socket joint 18.

Figure 2:
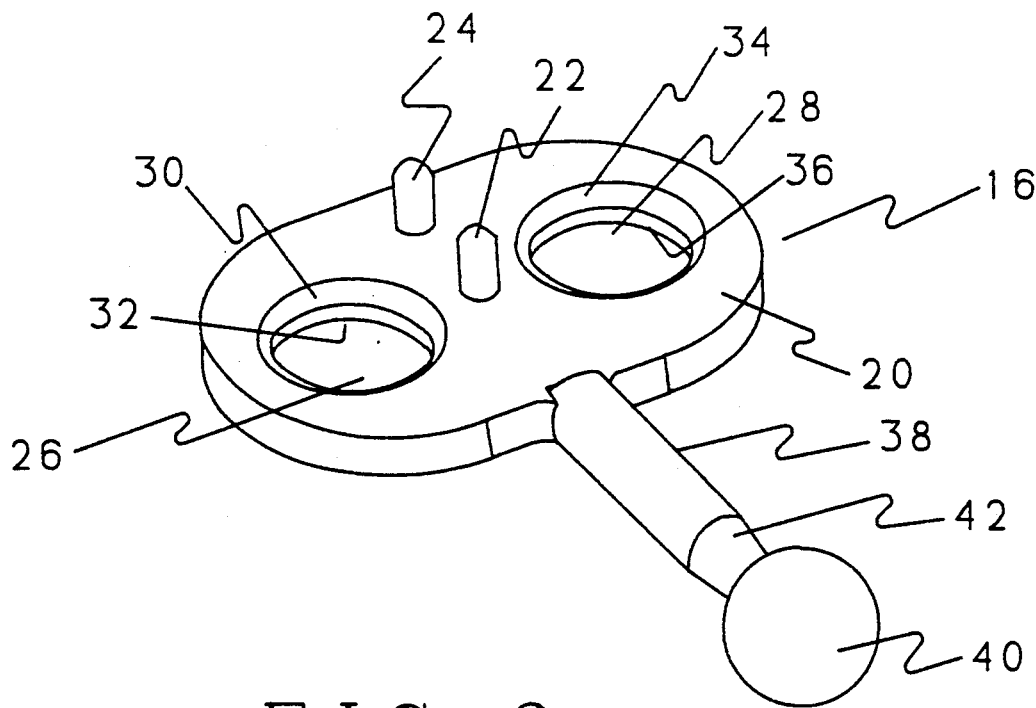
FIG. 2 is an enlarged perspective view of a template and ball joint.

As shown in FIG. 2, the template 16 comprises a symmetrical plate 20 having centrally disposed pins 22, 24. The pins 22, 24 can be driven into a resected bony surface when the template 16 is held against that surface. The pins 22, 24 secure the template 16 and prevent it from moving while bores are being made. To guide a drill bit, drill bores 26, 28 are provided in the template 16. The specific position and number of the bores is chosen to conform to a selected prosthesis which the surgeon intends to implant. The position of the bores 26, 28 is, therefore, merely illustrative. We prefer to provide bevels 30, 32, 34 and 36 on both sides of the bores 26, 28. These bevels make it easier to insert a drill bit.

A shaft 38 connects the plate 20 to a ball 40. A taper 42 between the shaft 38 and ball 40 increases the range of mobility of the template 16 in the universal joint 18, as will be more fully explained below.

Figure 4:
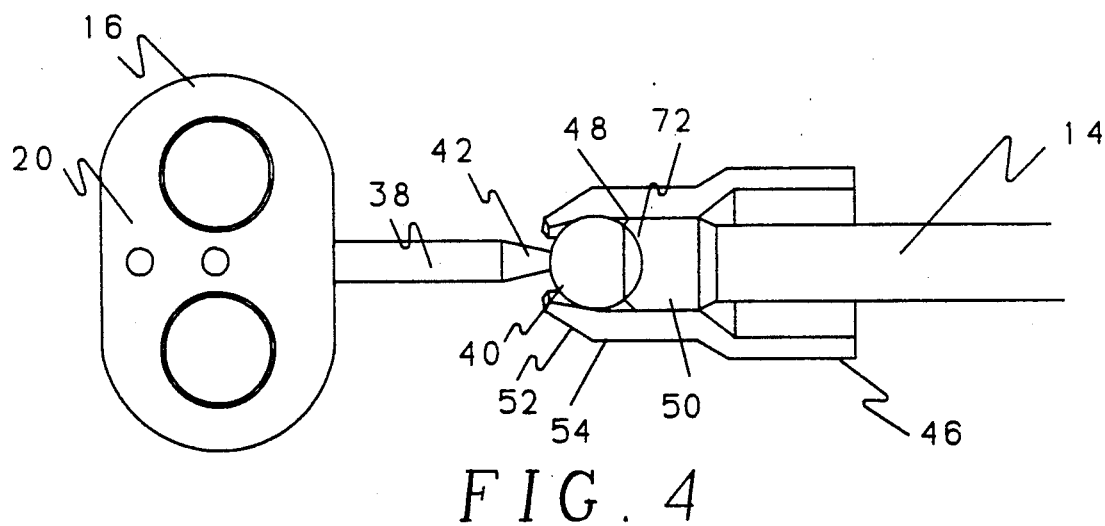
FIG. 4 is a through section of the cap and ball joint taken along line 4—4 in FIG. 1.
Figure 3:
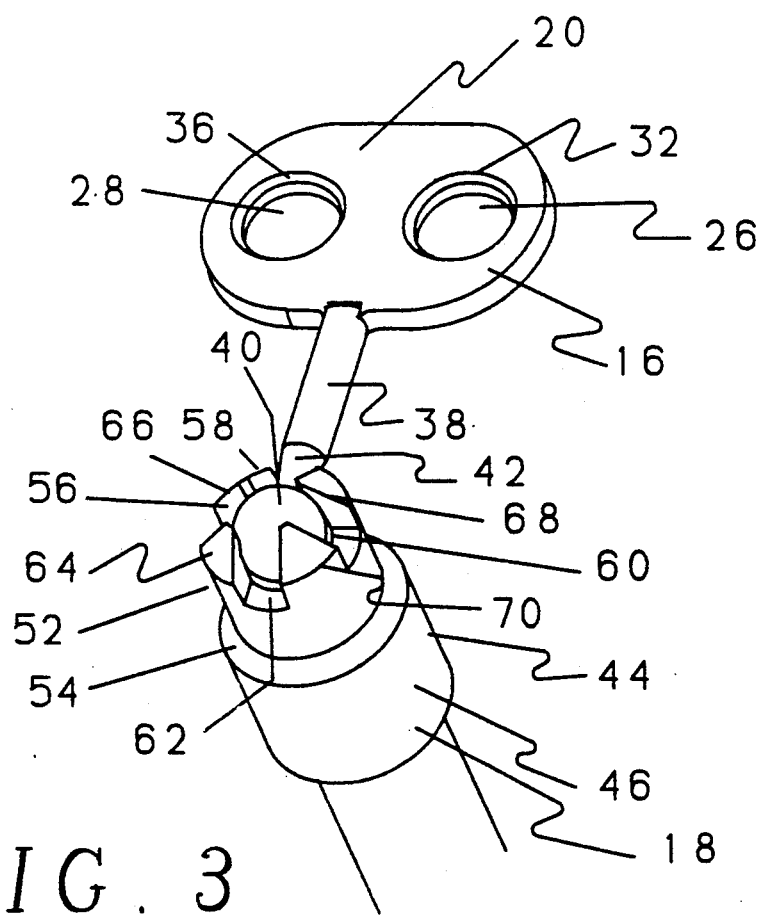
FIG. 3 is a perspective view of the template and ball joint of FIG. 2 engaged in a cap.

In FIG. 3, we have shown an enlarged perspective view of the template 16 and universal joint 18. The universal joint 18 comprises a nut 44 which has an enlarged cuff 46. A surgeon turns the cuff 46 to tighten the universal joint and lock the ball 40 in a selected position. As seen in the through section of FIG. 4, the bent shaft 14 has a threaded distal end 48 which engages internal threads 50 within the nut 44. A socket 52 at a distal end 54 of the nut captures the ball 40. Cruciate slots 56, 58, 60 and 62 allow the shaft 38 to positioned throughout hemispherical area with respect to the bent shaft 14. Because the template 16 can be inverted around the axis of the shaft 38, there is effectively a full spherical range of displacement. As can be seen in FIG. 3, the taper 42 makes it possible to have more narrow slots 56, 58, 60, 62, thus increasing the strength of fingers 64, 66, 68 and 70.

At the distal end of the shaft 14, we have made a recess 72 (shown in dotted line) which mates against the ball 40. When a surgeon tightens the nut 44, the ball 40 is compressed between the fingers 64, 66, 68 and 70 and the recess 72 in the distal end of the shaft. The ball is frictionally locked in a selected position. The drill guide can then be used to accurately place desired bores or cuts in any situation which might be encountered.

Our invention may be embodied in other specific forms without departing from the spirit or essential characteristics thereof. The present embodiment is therefore considered in all respects to be illustrative and not restrictive, the scope of our invention being indicated by the appended claims rather than by the foregoing description and all changes which come within the meaning and range of equivalency of the claims are therefor intended to be embraced therein.

We claim as our invention:

1. An orthopedic surgical drill guide for placement of drilled bores into a resected surface of a bone of a patient, said drill guide comprising
   means for guiding a bone-cutting surgical bit, said guiding means comprising a plate having at least one bore extending therethrough;
   a handle; and
   a ball and socket joint connecting said handle and said guiding means, said ball and socket joint comprising a nut threadedly engaging a distal end of said handle, said nut having an open distal end with a plurality of inwardly curved fingers extending distally therefrom, and
   a ball captured within said nut, said ball being rigidly connected to said guiding means.

2. The orthopedic surgical drill guide according to claim 1 wherein said distal end of said handle further comprises concave cavity adapted to mate with a part of said ball.

3. The orthopedic surgical drill guide according to claim 2 wherein the handle further comprises a curved shaft connecting said handle and said distal end.

4. The orthopedic surgical drill guide according to claim 3 wherein said nut further comprises means for tightening said nut on said distal end.

5. The orthopedic surgical drill guide according to claim 4 wherein the tightening means comprise a cuff having an enlarged radial dimension.

6. The orthopedic drill guide according to claim 5 wherein the drill guide further comprises at least one pin for temporarily securing said drill guide to bone.

* * * * *